(12) United States Patent
    Sabti

(10) Patent No.: US 9,474,596 B2
(45) Date of Patent: Oct. 25, 2016

(54) PRE-SHAPED SPIRAL INTRAOCULAR LENS FIXATION DEVICE

(71) Applicant: Khalid Sabti, Mubarak Al Abdulla (KW)

(72) Inventor: Khalid Sabti, Mubarak Al Abdulla (KW)

( * ) Notice: Subject to any disclaimer, the term of this patent is extended or adjusted under 35 U.S.C. 154(b) by 0 days.

(21) Appl. No.: 14/613,291

(22) Filed: Feb. 3, 2015

(65) Prior Publication Data

US 2016/0220353 A1    Aug. 4, 2016

(51) Int. Cl.
    *A61F 2/16*    (2006.01)
(52) U.S. Cl.
    CPC .............. *A61F 2/1662* (2013.01); *A61F 2/16* (2013.01); *A61F 2002/1681* (2013.01)
(58) Field of Classification Search
    CPC .. A61F 2/1662; A61F 2/1664; A61F 2/1667; A61F 2/167; A61F 2/1672; A61F 2/1675; A61F 2/1678
    See application file for complete search history.

(56) References Cited

U.S. PATENT DOCUMENTS

| 5,147,370 | A | | 9/1992 | McNamara et al. |
| 5,358,479 | A | * | 10/1994 | Wilson ................. 604/95.04 |
| 6,283,979 | B1 | | 9/2001 | Mers Kelly et al. |
| 7,867,267 | B2 | | 1/2011 | Sullivan et al. |
| 2008/0086854 | A1 | * | 4/2008 | Boyd et al. ............. 24/715.3 |
| 2010/0057202 | A1 | | 3/2010 | Bogaert |
| 2013/0237744 | A1 | | 9/2013 | Pfeffer et al. |

* cited by examiner

*Primary Examiner* — Thomas McEvoy
(74) *Attorney, Agent, or Firm* — Richard C. Litman

(57) ABSTRACT

The pre-shaped spiral intraocular lens fixation device has a hollow housing, the hollow housing having an elongate neck, an elongate handle, and a vacuum chamber. A selectively operable vacuum source is operatively attached to the housing to provide suction. A head is disposed at an end of the neck distal from the handle and a tubular structure is positioned within the hollow housing and extending through the neck out through the head. The tubular structure has a spiral-shaped position and can be made of a nitinol material. An actuating mechanism moves the tubular structure from a spiral-shaped position to a straight position.

1 Claim, 4 Drawing Sheets

PRE-SHAPED SPIRAL INTRAOCULAR LENS FIXATION DEVICE

BACKGROUND OF THE INVENTION

1. Field of the Invention

The present invention relates to ophthalmic surgery, and particularly to an intraocular lens fixation device using a nitinol pre-shaped spiral tube to align the lens in the eye.

2. Description of the Related Art

Intraocular lens fixation devices allow for the placement of a lens in the eye of a patient. In certain situations, the lens can have a need to be adjusted. Current intraocular lens fixation devices can be intrusive and difficult to manipulate the lens during surgery to implant the lens in the patient's eye. Further, these devices can be difficult to achieve rotational movement of the lens in the eye.

Thus, a pre-shaped spiral intraocular lens fixation device solving the aforementioned problems is desired.

SUMMARY OF THE INVENTION

The pre-shaped spiral intraocular lens fixation device includes a hollow housing. The hollow housing has an elongate neck, an elongate handle, and a vacuum chamber. A selectively operable vacuum source is operatively attached to the housing to provide suction. A head is disposed at an end of the neck distal from the handle, and a tubular structure is positioned within the hollow housing and extending through the neck out through the head. The tubular structure has a spiral-shaped region adjacent to the head, which can be made of nitinol tubing. An actuating mechanism is selectively movable and moves the tubular structure from a spiral-shaped position to a straight position.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
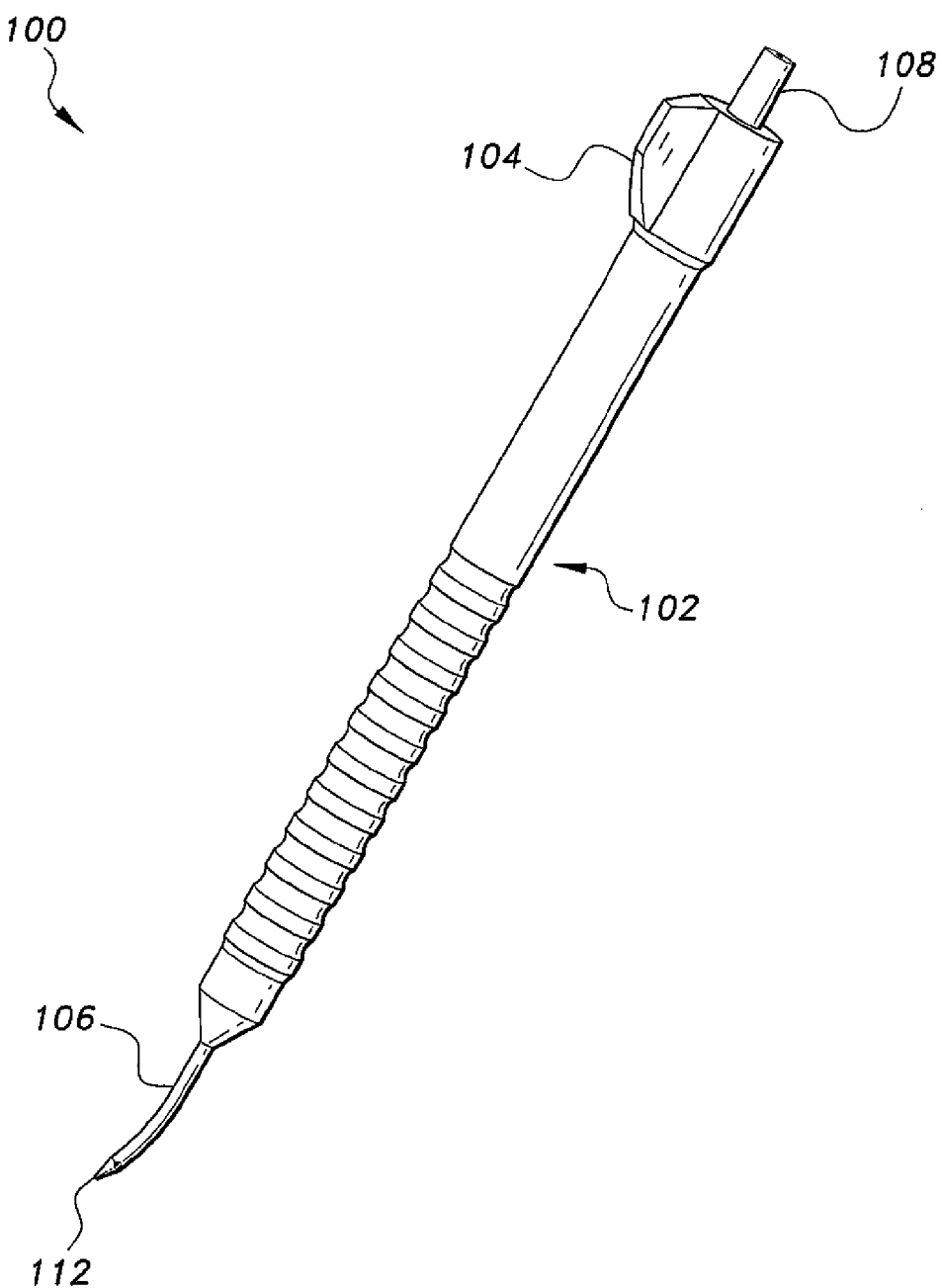
FIG. 1 is a perspective view of a first embodiment of a pre-shaped spiral intraocular lens fixation device according to the present invention.

Referring to FIG. 1, a pre-shaped spiral intraocular lens fixation device 100 is shown. The pre-shaped spiral intraocular lens fixation device 100 has a hollow housing 102. At an end of the housing 102 is a handle 104 and remote from the handle 104 is a neck 106. The handle 104 can be manipulated by an operator and can be any suitable shape, such as a knob. The neck 106 can be straight or curved, depending on the user's needs. A vacuum chamber 108 is included in the housing 102 and can be in communication with a vacuum source. A head region 112 of the neck is positioned adjacent to the neck 106 and allows for communication between the patient and the housing 102.

Figure 2A:
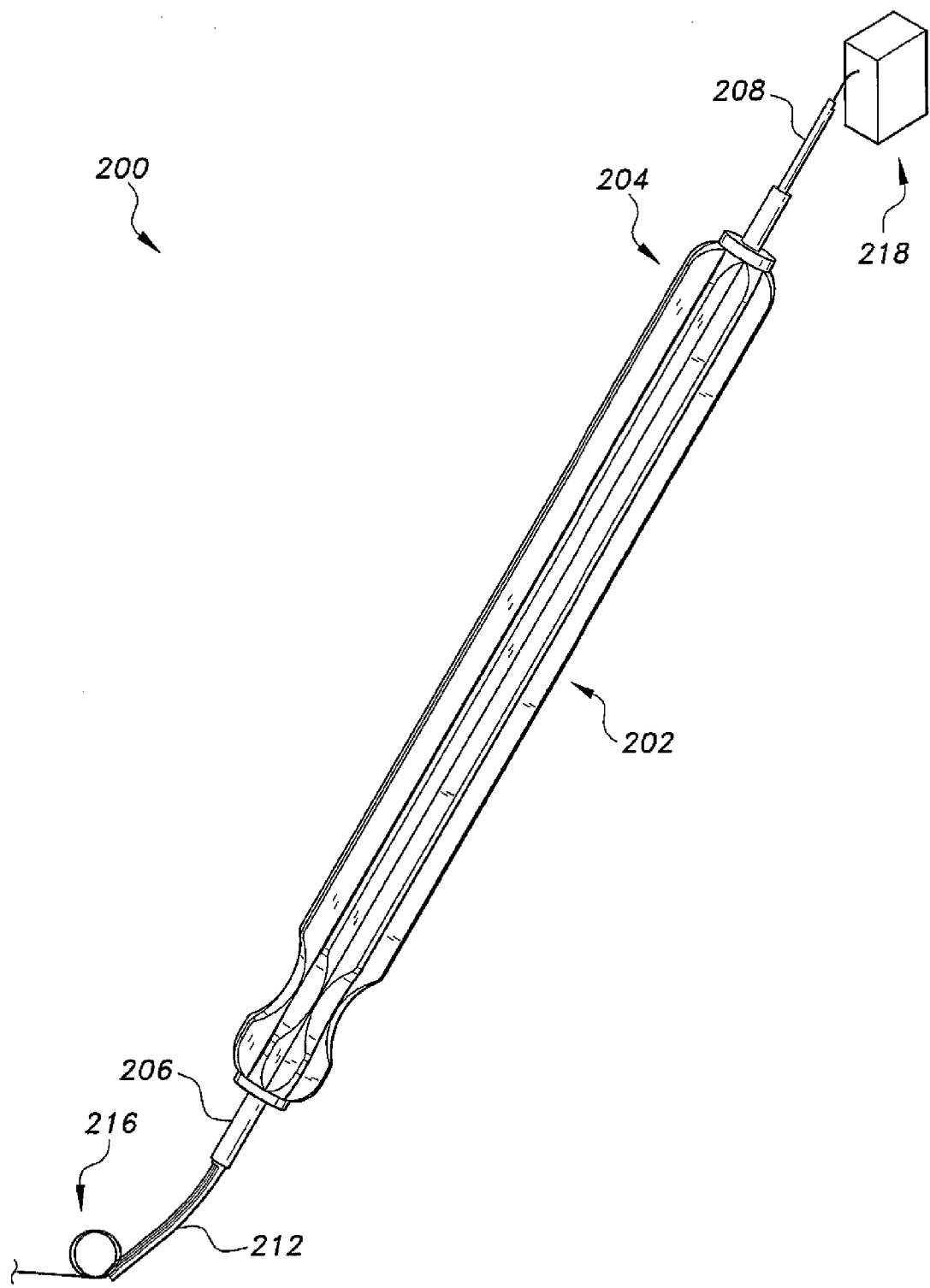
FIGS. 2A and 2B are perspective views of a second embodiment of a pre-shaped spiral intraocular lens fixation device according to the present invention, shown with the spiral region coiled and extended, respectively.
Figure 2B:
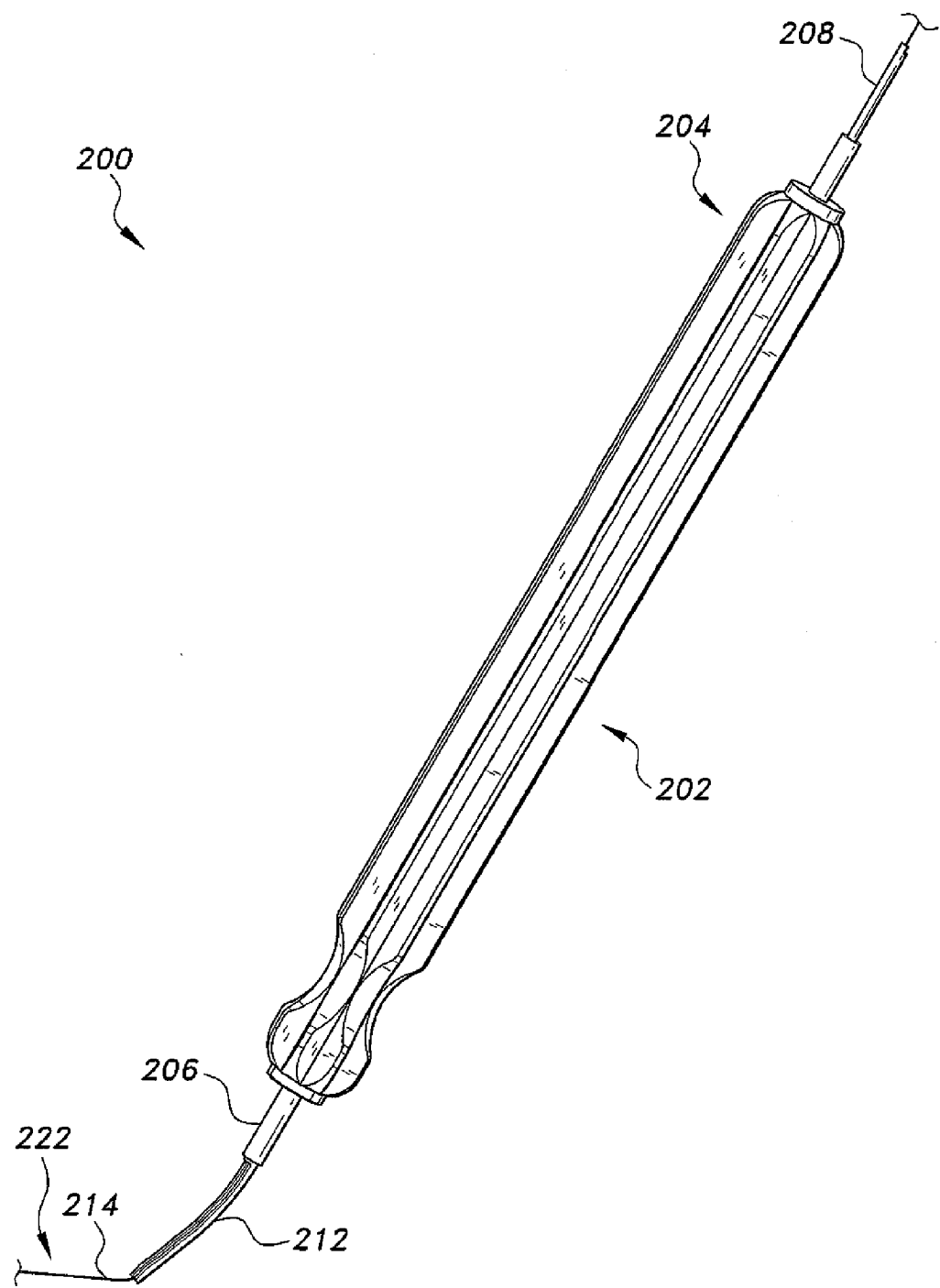

Referring to FIGS. 2A and 2B, another embodiment of a pre-shaped spiral intraocular lens fixation device 200 is shown. Similar to pre-shaped spiral intraocular lens fixation device 100, the pre-shaped spiral intraocular lens fixation device 200 has a hollow housing 202, a handle 204, a neck 206, a vacuum chamber 208, and a head 212. A tubular structure 214 extends through the hollow housing 202, through the neck 206, and out the head 212. The tubular structure 214 can be a wire used in medical procedures, for example. Further, the wire can be composed of various materials, such as nitinol for example. The nitinol material can be a Nitinol 2D flat structure.

As shown in FIG. 2A, the tubular structure 214 includes a pre-shaped spiral region 216. The pre-shaped spiral region 216 is adjacent to the head 212 and remote from the handle 204. An actuating mechanism 218 allows for a user to actuate the tubular structure 214 from a pre-shaped spiral position 216 to a straight position 222, as shown in FIG. 2B. The actuating mechanism 218 can be a dial, an operator's hand, or any other suitable mechanism. By actuating the tubular structure 214 from a spiral position 216 to a straight position 222, a rotational displacement is created. This rotational displacement allows for a lens to be rotated onto a patient's eye by transforming longitudinal displacement to rotational displacement.

Figure 3:
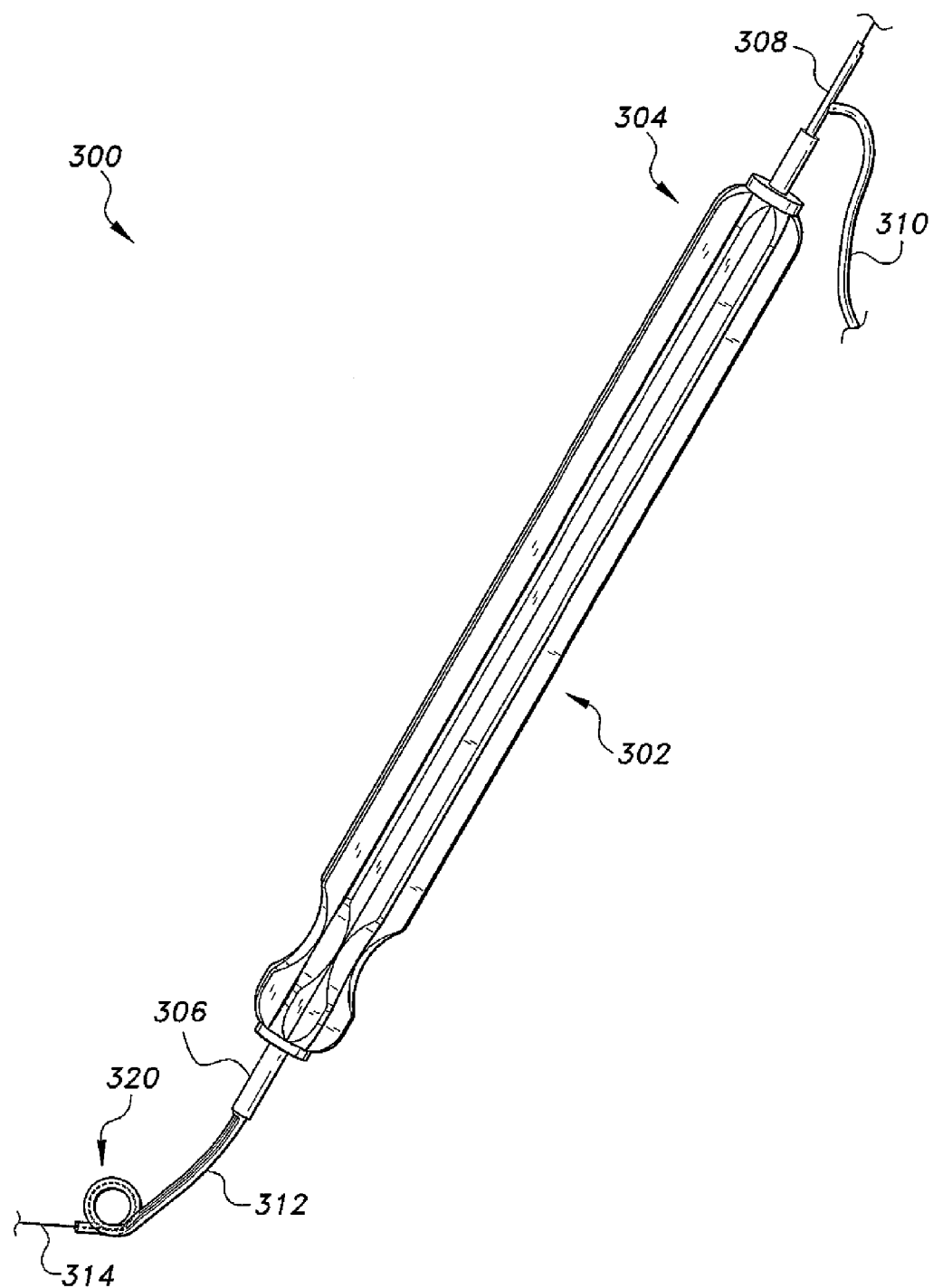
FIG. 3 is a perspective view of a third embodiment of a pre-shaped spiral intraocular lens fixation device according to the present invention where the tubular structure has been actuated.

Referring to FIG. 3, another embodiment of a pre-shaped spiral intraocular lens fixation device 300 is shown. Similar to the pre-shaped spiral intraocular lens fixation device 100 and 200, the pre-shaped spiral intraocular lens fixation device 300 includes a hollow housing 302, a handle 304, a neck 306, a vacuum chamber 308, a head 312, and a tubular structure 314. The tubular structure can have a pre-shaped spiral positon and a straight position. As shown in FIG. 3, positioned in conjunction with the tubular structure 314 is a suction cup 320. The suction cup 320 is in communication with the vacuum chamber 308, which receives a suction force from the vacuum source 310. The vacuum source can be any pressurized source, such as a pump. The suction cup 320 can be made from a number of materials, such as medical grade plastic, for example. The suction cup 320 allows for an object, such as an intraocular lens, to be snared up from the eye of a patient, among other objects. Similar to the pre-shaped spiral intraocular lens fixation device 200, actuating the tubular structure 300 allows for the pre-shaped spiral position to be changed to a straight position. By actuating the tubular structure 300, the suction cup 320 can also be actuated from a pre-shaped spiral position to a straight position.

It is to be understood that the present invention is not limited to the embodiments described above, but encompasses any and all embodiments within the scope of the following claims.

I claim:

1. A pre-shaped spiral intraocular lens fixation device in combination with an intraocular lens, the combination comprising:
    a hollow housing having an elongate neck and an elongate handle remote from the elongate neck, the hollow housing having a vacuum chamber;
    a head disposed at an end of the neck distal from the handle;
    a selectively operable vacuum source operatively attached to the housing and in communication with the vacuum chamber;

a tubular structure positioned within the hollow housing and extending through the neck out through the head, the tubular structure being in communication with the vacuum chamber, the tubular structure having a spiral-shaped position adjacent to the head, the tubular structure consisting of a nitinol material;

a suction cup positioned in conjunction with the spiral-shaped region of the tubular structure;

an actuating mechanism in communication with the tubular structure, the actuating mechanism being selectively movable;

wherein selective movement of the actuating mechanism selectively moves the tubular structure between a spiral-shaped position and a straight position; and an intraocular lens;

wherein the handle is manipulated to control the elongate neck, the head, the tubular structure, and the actuating mechanism for positioning, dispensing and fixating the intraocular lens.

* * * * *